United States Patent [19]
Sninsky et al.

[11] Patent Number: 5,386,022
[45] Date of Patent: Jan. 31, 1995

[54] PRIMES AND PROBES FOR THE AMPLIFICATION AND DETECTION OF AIDS ASSOCIATED NUCLEIC ACIDS

[75] Inventors: John J. Sninsky, El Sobrante; Shirley Y. Kwok, San Ramon, both of Calif.; David Mack, Chicago, Ill.; Henry A. Erlich, Oakland; Kary B. Mullis, LaJolla, both of Calif.

[73] Assignee: Hoffmann-LaRoche Inc., Nutley, N.J.

[21] Appl. No.: 92,767

[22] Filed: Jul. 16, 1993

Related U.S. Application Data

[60] Continuation of Ser. No. 918,907, Jul. 22, 1992, abandoned, which is a continuation of Ser. No. 639,103, Jan. 9, 1991, abandoned, which is a continuation of Ser. No. 394,276, Aug. 15, 1989, Pat. No. 5,008,182, which is a continuation of Ser. No. 935,581, Nov. 26, 1986, abandoned, which is a continuation-in-part of Ser. No. 818,127, Jan. 10, 1986, abandoned, which is a continuation-in-part of Ser. No. 828,144, Feb. 7, 1986, Pat. No. 4,683,195, which is a continuation of Ser. No. 824,044, Jan. 30, 1986, abandoned, which is a division of Ser. No. 791,308, Oct. 25, 1985, Pat. No. 4,683,202, which is a continuation-in-part of Ser. No. 716,975, Mar. 28, 1985, abandoned.

[51] Int. Cl.$^6$ .................. C07H 21/04; C12Q 1/70; C12Q 1/68; C12P 19/34
[52] U.S. Cl. .................. 536/24.32; 536/24.3; 435/5; 435/6; 435/91.2
[58] Field of Search .................. 435/6, 91.1, 91.2, 5; 536/24.32, 24.3

[56] References Cited

U.S. PATENT DOCUMENTS

| | | | |
|---|---|---|---|
| 4,652,599 | 3/1987 | Gallo | 435/239 |
| 4,683,195 | 7/1987 | Mullis et al. | 435/6 |
| 4,683,202 | 7/1987 | Mullis | 435/91 |
| 4,716,102 | 12/1987 | Levy | 435/5 |

FOREIGN PATENT DOCUMENTS

| | | |
|---|---|---|
| 062286 | 10/1982 | European Pat. Off. |
| 120658 | 10/1984 | European Pat. Off. |
| 178978 | 4/1986 | European Pat. Off. |
| 229701 | 7/1987 | European Pat. Off. |
| 8604146 | 7/1986 | WIPO ............ 435/6 |

OTHER PUBLICATIONS

Barre-Sinoussi et al., 1983, Science, 230:868–871.
Brun-Vezinet et al., 1984, Science, 226:453–456.
Kobayashi et al., 1984, EMBO J., 3:1339–1343.
Luciw, et al. 1984, Nature, 312:760–763.
Meusing et al., 1985, Nature, 313:450–458.
Ratner et al., 1985, Nature, 313:277–284.
Sanchez-Pescador et al., 1985, Science, 227:484–492.
Starcich et al., 1985, Science, 227:538–546.
Wain-Hobson et al., 1985, Cell, 40:9–17.
Shaw et al., 1984, PNAS (USA), 81:4544–4548.
Sauls & Caskey, 1985, Clin. Chem., 31:804–811.
Starich et al., 1986, Cell, 45:637–648.
Kwok et al., 1987, J. Virol., 61:1690–1694.

*Primary Examiner*—Stephanie W. Zitomer
*Attorney, Agent, or Firm*—George M. Gould; Stacey R. Sias; Doug Petry

[57] ABSTRACT

The presence or absence of a nucleic acid sequence associated with AIDS in a sample containing one or more nucleic acids and suspected of containing such sequence can be detected by amplifying the sequence using primers to form extension products as templates and detecting the amplified product if it is present. This may be accomplished by adding a labeled hybridization probe to the amplified product either free in solution or after immobilization on a solid support. Exemplary primers and probes for amplifying and detecting AIDS virus are provided.

8 Claims, 3 Drawing Sheets

*= LABEL

✶ = LABEL

FIG. 2

```
     |————————SK07————————————————|
5' GATCCGAGAGAACCAAGGGGAAGTGACATAGCAGGAACTACTAGTACC
   GCTCTCTTGGTTCCCCTTCACTGTATCGTCCTTGATGATCATGG
     |————————————SK16————————————|

|————————SK08————————————————|
   CTTCAGGAACAAATAGGATGGATGACAAATAATCCACCTATCCCAGT
   GAAGTCCTTGTTTATCCTACCTACTGTTTATTAGGTGGATAGGGTCA
     |————————SK15————————————|

|————————SK09————————————————|
   AGGAGAAATCTATAAAAGATGGATAATCCTGGGATTAAATAAAATA
   TCCTCTTTAGATATTTTCTACCTATTAGGACCCTAATTTATTTTAT
     |————————————SK14————————————|

|———SK10———|    |————SK11————|
   GTAAGAATGTATAGCCCTACCAGCATTCTGGACATAAGACAAGGG 3'
   CATTCTTACATATCGGGATGGTCGTAAGACCTGTATTCTGTTCCCCTAG
     |————SK13————|        |————SK12————|
```

FIG. 3
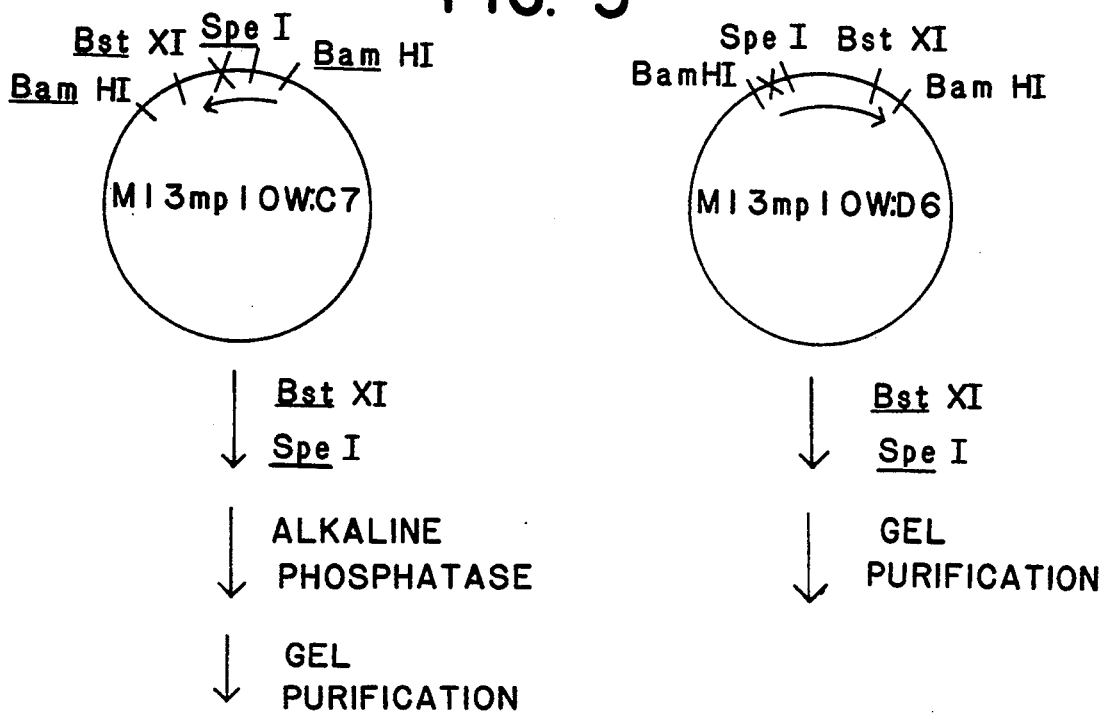
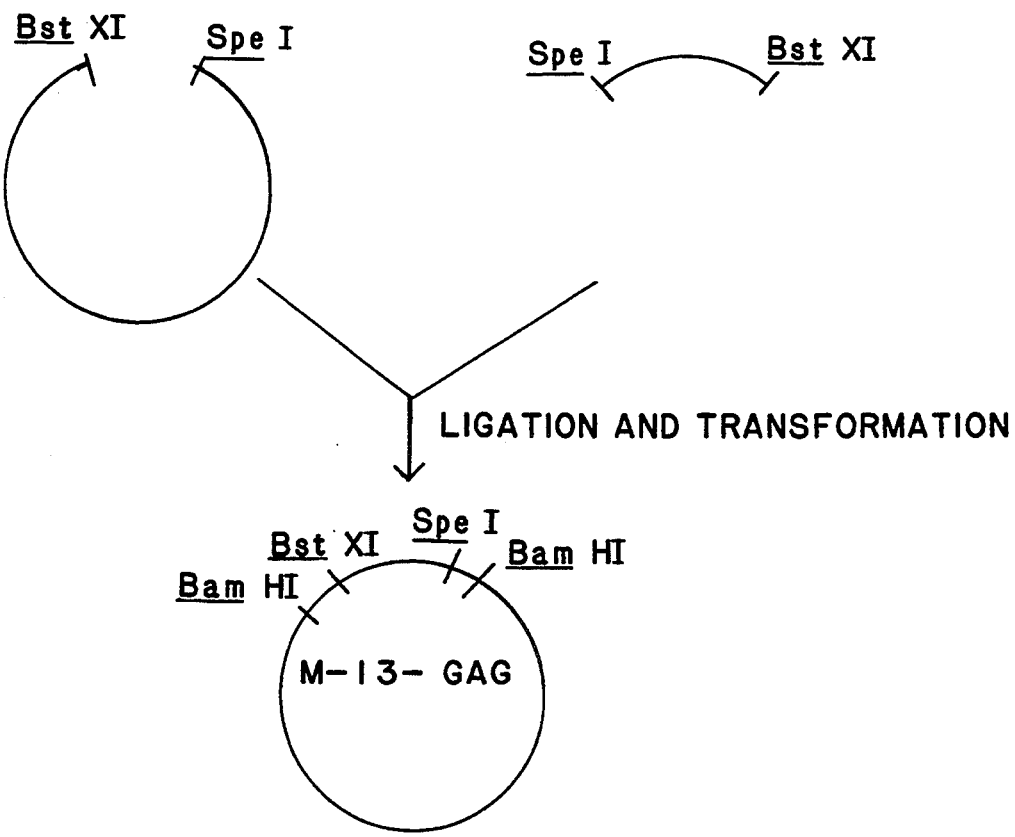

PRIMES AND PROBES FOR THE AMPLIFICATION AND DETECTION OF AIDS ASSOCIATED NUCLEIC ACIDS

CROSS REFERENCE TO RELATED APPLICATIONS

This application is a continuation of application Ser. No. 07/918,907, filed Jul. 22, 1992, now abandoned, which is a continuation, of application Ser. No. 07/639,103, filed Jan. 9, 1991, now abandoned, which is a continuation of U.S. Ser. No. 394,276filed Aug. 15, 1989, which issued as U.S. Pat. No. 5,0008,182, which is a continuation of U.S. Ser. No. 935,581, filed Nov. 26, 1986, now abandoned, which is a continuation-in-part application of U.S. Ser. No. 818,127, filed Jan. 10, 1986, now abandoned. U.S. Ser. No. 394,276, is also a continuation-in-part application of U.S. Ser. No. 828,144, filed Feb. 7, 1986, which issued as U.S. Pat. No. 4,683,195 on Jul. 28, 1987, which is a continuation-in-part of U.S. Ser. No. 824,044, filed Jan. 30, 1986, now abandoned, which is a divisional of U.S. Ser. No. 791,308, filed Oct. 25, 1985, which issued as U.S. Pat. No. 4,683,202 on Jul. 28, 1987, and which is a continuation-in-part of U.S. Ser. No. 716,975, filed Mar. 28, 1985, now abandoned.

BACKGROUND OF THE INVENTION

The present invention relates to a process for detecting the presence or absence of a conserved, nucleotide sequence of a virus associated with acquired immune deficiency syndrome (AIDS). This invention also relates to a kit for such detection having primers and a labeled hybridization probe.

The acquired immune deficiency syndrome (AIDS) is a transmissible disorder of the cellular immune system resulting in frequently fatal opportunistic infections or neoplasms. In addition, AIDS is frequently complicated by central nervous system dysfunction. The aetiologic agent(s) responsible for this disease has been identified as a human retrovirus and designated as human T cell leukemia virus III (HTLVIII), lymphadenopathy associated virus (LAV or LAVA ), and AIDS-associated virus (ARV-2). More recently these viruses have been collectively referred to as human immunodeficiency virus (HIV). The isolates from the various laboratories represent identical or closely related viruses by numerous criteria (i.e., morphology, immunological cross-reactivities of envelope and nucleocapsid proteins, nucleotide sequence, and entry into helper T cells using the T4 antigen). A simian virus isolated from chimpanzees and macaques suffering from symptoms indistinguishable from AIDS in humans is also closely related by these same criteria. P. J. Kanki et al., *Science,* 230:951-954 (1985).

One of the more intriguing observations about the viruses associated with AIDS is their resemblance to the mature virion of subfamily Lentiviridae. Members of this pathogenic but non-oncogenic viral group include visna virus, and equine infectious anemia virus. The similarities between the AIDS-associated viruses and lentiviruses include virion morphology, immunological cross-reactivity, nucleotide sequence, brain localization, replication, .and marked heterogeneity.

The current immunodiagnostic tests to identify sera with antibodies to the AIDS-associated virus(es) (see U.S. Pat. No. 4,520,113 to Gallo et al.) are being used in blood banks to eliminate potentially infectious blood. See also WO 86/01834 published Mar. 27, 1986 (University of California) for retroviral polypeptides useful in preparing monoclonal antibodies to detect retroviruses in the HTLV family. Because the similarities of the AIDS-associated viruses and lentiviruses, in general, or visna specifically, may extend to the ability of the virus(es) to reside as a DNA copy without producing significant quantities of viral particles, a direct immunological approach to detect AIDS-associated viruses may prove unsuccessful in a significant fraction of persistently infected asymptomatic individuals. Because the number of virus particles in the infected tissues and blood may be few (due to viral quiescence), direct detection of viral particles or RNA/DNA may be difficult, if not impossible, without co-culturing the infected cells with a permissive T cell line. Even with co-cultivation, the number of individuals infected by HIV as indicated by virus isolation is an underestimate of the true number of infected individuals; virus from only 50% AIDS patients, 85% of ARC, and 30% of healthy individuals at risk for AIDS was isolated (Salahuddin et al., *PNAS USA,* 82, 5530–4 (1985)).

U.S. Pat. No. 4,683,202 by inventor K. Mullis describes a process for amplifying nucleic acid sequences to facilitate detection thereof, as by using a labeled RNA or DNA hybridization probe. In this process primers are used to obtain primer extension products which are used as templates to synthesize additional complementary strands in the presence of nucleotides. The above-mentioned patent application also describes a technique whereby after a probe is hybridized to the desired sequence, a restriction enzyme is added to cleave the hybrid at a site within the desired sequence, and the restriction digest is then analyzed for labeled fragments. U.S. Pat. No. 4,683,195 by inventors H. Erlich et al. and Saiki et al., *Biotechnology,* 3:1008–1012 (1985) describe this latter technique in greater detail. Both patent applications illustrate use of the process for detecting genetic diseases such as sickle cell anemia and β-thalassemia. These methods and the process for amplifying nucleic acid sequences are also disclosed in Saiki et al., *Science,* 230, 1350–1354 (1985), the disclosure of which is incorporated herein by reference. This application is related to U.S. Ser. No. 394,145, filed Aug. 15, 1989, which is a continuation of U.S. Ser. No. 934,955, filed Nov. 26, 1986, entitled, "Detection of Viruses by Amplification and Hybridization," now abandoned, which is a continuation in part of 818,127 filed Jan. 10, 1987, now abandoned.

A review article by Landry et al., *Clin. Lab. Med.* (1985) 5, 513–529 describes the field of nucleic acid hybridization as applied to virus detection. WO86/01535 published Mar. 13, 1986 and EP 173,529 published Mar. 5, 1986 disclose molecular cloning of HTLVIII and use of the clone as a probe to detect AIDS. Further, EP patent publication 173,339, published Mar. 5, 1986, discloses a genetic analysis using a DNA probe to detect infections by foreign microbes. EP 185,444, published Jun. 25, 1986, discloses a recombinant peptide for use as a probe to detect the HTLVIII virus in cell lysates. Oncor Inc. announced in September, 1986 that it has developed a radioactive blood test to detect the AIDS virus.

Use of a hybridization probe to detect AIDS may allow identification of those individuals who are persistently infected but are not producing virus or individuals who are antibody negative but culture positive, and to detect infected cells without the need to culture the virus. Increasing the viral nucleic acid copy number of the virus by amplification will facilitate the identification of viral nucleic acid in infected individuals.

SUMMARY OF THE INVENTION

The present invention involves a process for detecting or monitoring for the presence or absence of a nucleic acid sequence which is substantially conserved among the nucleic acids in AIDS viruses and specific to the nucleic acids in HIV (AIDS viruses) and which nucleic acid sequence is suspected of being contained in a sample, which process comprises:

(a) treating the sample, together or separately, with an oligonucleotide primer for each strand of the nucleic acid sequence, four different nucleoside triphosphates, and an agent for polymerization, under hybridizing conditions, such that for each strand of the nucleic acid sequence an extension product of each primer is synthesized which is complementary to each nucleic acid strand, wherein said primer(s) are substantially complementary to each strand of the nucleic acid sequence being detected or monitored, such that the extension product synthesized from one primer, when it is separated from its complement, can serve as a template for synthesis of the extension product of the other primer;

(b) treating the sample under denaturing conditions;

(c) treating the product of step (b) with oligonucleotide primers such that a primer extension product is synthesized using each of the single strands produced in step (b) as a template, resulting in amplification of the specific nucleic acid sequence or sequences if present; and (d) determining if the sequence to be detected is present in the sample.

One way to detect the product is by adding to the product of step (c) a labeled probe capable of hybridizing with the amplified nucleic acid sequence; and determining whether the probe has hybridized to an amplified sequence in the nucleic acid sample. In one embodiment, this determination can be made by:

(1) digesting the hybridized mixture with a restriction enzyme recognizing a site within the sequences in the probe; and (2) detecting whether the restriction digest contains a restriction fragment correlated with the presence of the AIDS sequence.

Before step (a) the nucleic acids in a patient sample may be extracted therefrom so that the sample being treated is actually the mixture of the extracted nucleic acids. In addition, the sample being treated in step (a) need not be subjected beforehand to a process wherein the virus in the sample is cultured.

In another embodiment, the invention herein relates to a kit for detecting or monitoring for the presence or absence of a nucleic acid sequence which is substantially conserved among the nucleic acids in AIDS viruses and specific to the nucleic acids in AIDS viruses and which nucleic acid sequence is suspected of being contained in a sample, which kit comprises:

(a) one oligonucleotide primer for each strand of the nucleic acid sequence to be detected, which primer or primers are substantially complementary to each strand of each specific nucleic acid sequence such that an extension product synthesized from one primer, when it is separated from its complement, can serve as a template for the synthesis of the extension product of the other primer; and (b) a labeled probe capable of hybridizing with the nucleic acid sequence.

Preferably, the kit also contains an agent for polymerization, four different nucleotides, and a means for detecting hybrids of the probe and sequence.

The test kit herein may be used in research tests, clinical tests and other diagnostic applications. In addition, it can be used to detect infected cells without culturing the virus, a feature useful in monitoring patients treated with various therapeutic agents to resolve the infection.

BRIEF DESCRIPTION OF THE DRAWINGS

FIG. 2 is a schematic representation of ten oligonucleotides of the HIV sequence which were ligated together to form a 180 bp DNA fragment for a hybridization probe to be used in dot blots to detect amplified products.

FIG. 3 is a schematic flow diagram of how two clones, M13mp10W:C7 and M13mp10W:D6, which contain nucleotide sequence alterations, were treated to obtain a sequence identical to HIV. The resulting clone, M-13-GAG, contains the 180 bp insert for use as a hybridization probe in dot blots. In the FIG., X denotes mutation in the gene.

DETAILED DESCRIPTION OF THE PREFERRED EMBODIMENTS

Figure 1:
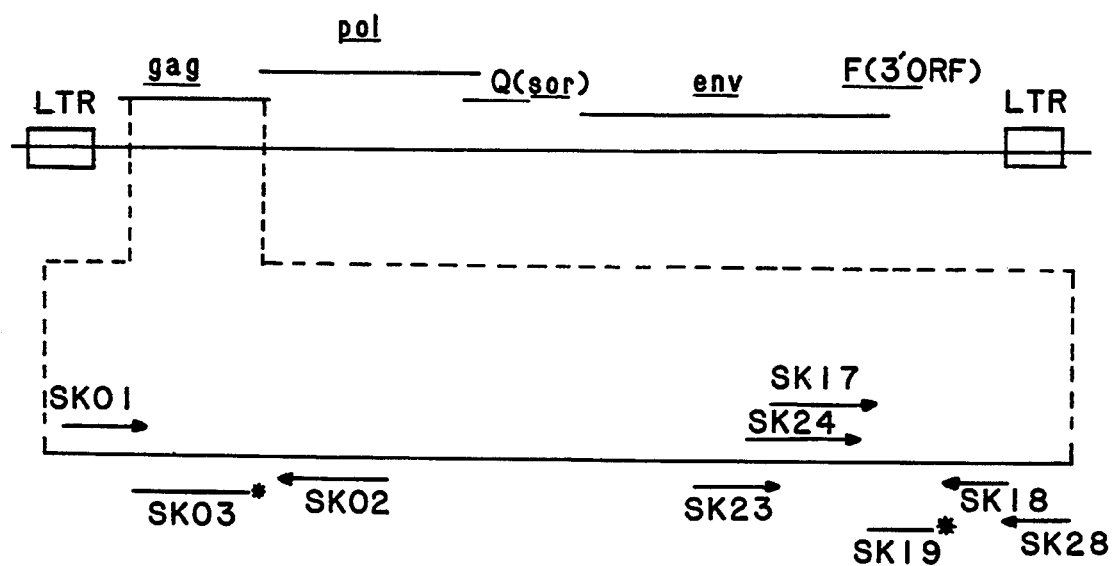
FIG. 1 is a schematic representation of the entire HIV genome, which consists of the long terminal repeat (LTR) noncoding regions and the gag, pol, env, Q (or sor) and F (or 3'ORF) coding regions, and shows from what region the primers were chosen for the examples herein.

The present invention relates to a process and kit for detecting or monitoring for a nucleic acid sequence associated with HIV in a sample of nucleic acid(s) suspected of containing the sequence. Because the HIV is highly variable, there is a need to find a common denominator (conserved region with a length which allows specific primers as defined herein to initiate polymerization) among the virus variants to use for detecting a significant fraction of the viruses associated with AIDS. A significant fraction is that number of individuals sufficient to make the test diagnostically or commercially feasible. Currently four HIVs, ARV, HTLVIII, LAV and LAVA, have been sequenced. These four initial HIVs and their associated variants are designated herein as "AIDS viruses". The sequence to be amplified also must be specific to the AIDS viruses, i.e., not react with HTLVI or HTLVII or other non-AIDS viruses.

The entire genome of the four HIV isolates and their variants is provided by Sanchez-Pescador et al., *Science,* 227, 484–492 (1985) for ARV; Starcich et al., *Science,* 227, 538–540 (1985) for HTLVIII; Wain-Hobson et al., *Cell,* 9–17 (1985) for LAV; and Muesing et al., *Nature,* 313, 450–458 (1985) for LAVA. There is a general consensus that these viruses are all variants of the same strain.

The term "substantially conserved" as applied to the sequence to be detected signifies that the sequence must be sufficiently complementary to the nucleic acids in the virus being detected to initiate polymerization at least at room temperature in the presence of an agent for polymerization and the four nucleoside triphosphates.

The primers used will be oligonucleotides of any length and sequence so as to provide specific initiation of polymerization on a significant number of nucleic acids in AIDS viruses. Specifically, the term "primer" as used herein refers to a molecule comprised of two or more deoxyribonucleotides or ribonucleotides, preferably more than three, which is capable of acting as a point of initiation of synthesis when placed under conditions in which synthesis of a primer extension product which is substantially complementary to a nucleic acid strand is induced, i.e., in the presence of nucleoside triphosphates and an agent for polymerization such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact lengths of the primers will depend on many factors, including temperature, buffer, nucleotide composition and source of primer. For purposes herein, the oligonucleotide primer typically contains 15–25 or more nucleotides, although it may contain fewer nucleotides. Preferably the primer is from the gag region.

The primers herein are selected to be "substantially" complementary to each strand of the specific sequence to be amplified. This means that the primers must be sufficiently complementary to hybridize with their respective strands under conditions which allow the agent for polymerization to perform, i.e., the primers have sufficient complementarity with the sequence of the strand to be amplified to hybridize therewith and thereby form a template for synthesis of the extension product of the other primer. Preferably, the primers have exact complementarity with the strand.

One may select the sequence being amplified from among the regions that are substantially conserved among the AIDS viruses. Therefore, the primers and probes may be identified by any suitable means. This may be done manually by comparing the regions of the published nucleic acid sequences of the four AIDS viral genomes. Another more convenient method is to use a computer program to compare the sequences. For this purpose, a commercial program with the underlying computer algorithm supplied by National Biomedical Research Foundation using a dot matrix may be conveniently employed. This program involves inputting the nucleic acid sequences of the AIDS viruses and defining a window size for base pair homology. The program employs graphics to compare the sequences on different axes, and a dot appears where there is at least substantial homology. Preferably, the window size is greater than six bases.

A dot matrix program reveals that the gag region of the genome (see FIG. 1), also known as the nucleocapsid gene, is most conserved among the coding regions in the four variants. The next most conserved coding region is the pol region, followed by the env region of the genome. Because gag is most conserved among the coding regions, it is the preferred region from which to select primers and probes for detecting the sequence. Regions of the viral genome that do not encode proteins can also be used to determine a sequence for the primers to be used. For purposes herein, to maximize sensitivity and specificity, the sequence being detected is homologous with a sequence of a length sufficient to allow specific priming which is substantially conserved among the related viruses, particularly at the restriction cleavage site if a probe and restriction enzyme are employed.

The techniques used for amplifying and thereafter detecting the product are described in detail in U.S. Pat. Nos. 4,683,195 and 4,683,202, Saiki et al., *Biotechnology, supra* and Saiki et al., *Science,supra*, the entire disclosures of which are incorporated herein by reference. In general, the amplification process involves an enzymatic chain reaction for preparing, in exponential quantities relative to the number of reaction steps involved, a specific nucleic acid sequence, given that the ends of the required sequence are known in sufficient detail that oligonucleotide primers can be synthesized which will hybridize to them, and that a small amount of the sequence is available to initiate the chain reaction. One primer is complementary to the negative (−) strand and the other is complementary to the positive (+) strand. Annealing the primers to denatured nucleic acid followed by extension with an enzyme such as the large fragment of DNA Polymerase I (Klenow) and nucleotides results in newly synthesized + and − strands containing the target sequence. Because these newly synthesized sequences are also templates for the primers, repeated cycles of denaturing,, primer annealing and extension results in exponential accumulation of the region defined by the primer. The product of the chain reaction will be a discrete nucleic acid duplex with termini corresponding to the ends of the specific primers employed.

The amplification process is illustrated diagrammatically below, where double-stranded DNA containing the desired sequence [S] comprised of complementary strands [S+] and [S−] is utilized as the nucleic acid. During the first and each subsequent reaction cycle extension of each oligonucleotide primer on the original template will produce one new ssDNA molecule product of indefinite length which terminates with only one of the primers. These products, hereafter referred to as "long products," will accumulate in a linear fashion; that is, the amount present after any number of cycles will be proportional to the number of cycles.

The long products thus produced will act as templates for one or the other of the oligonucleotide primers during subsequent cycles and will produce molecules of the desired sequence [S+] or [S−] These molecules will also function as templates for one or the other of the oligonucleotide primers, producing further [S+] and [S$^{31}$ ], and thus a chain reaction can be sustained which will result in the accumulation of [S] at an exponential rate relative to the number of cycles.

By-products formed by oligonucleotide hybridizations other than those intended are not self-catalytic and thus accumulate at a linear rate.

The specific sequence to be amplified, [S], can be depicted diagrammatically as:

[S+]  5′ AAAAAAAAAAXXXXXXXXXXCCCCCCCCCC  3′
[S−]  3′ TTTTTTTTTTYYYYYYYYYYGGGGGGGGGG  5′

The appropriate oligonucleotide primers would be:

Primer 1:  3′ GGGGGGGGGG  5′
Primer 2:  5′ AAAAAAAAAA  3′ so that if DNA containing [S]

```
.... zzzzzzzzzzzzzzzzAAAAAAAAAAXXXXXXXXXXCCCCCCCCCCzzzzzzzzzzzzzzzz ....
.... zzzzzzzzzzzzzzzzTTTTTTTTTTYYYYYYYYYYGGGGGGGGGGzzzzzzzzzzzzzzzz ....
``` is separated into single strands and its single strands are hybridized to Primers 1 and 2, the following extension reactions can be catalyzed by DNA polymerase in the presence of the four deoxyribonucleoside triphosphates:

```
                                              3'                                                    5'
                extends  ⟵─────────────────── GGGGGGGGGG  Primer 1
.... zzzzzzzzzzzzzzzzAAAAAAAAAAXXXXXXXXXXCCCCCCCCCCzzzzzzzzzzzzzzzz ....
original template strand+ original template strand−
.... zzzzzzzzzzzzzzzzTTTTTTTTTTYYYYYYYYYYGGGGGGGGGGzzzzzzzzzzzzzzzz ....
        Primer 2      AAAAAAAAAA  ───────────────⟶ extends
                      5'         3'
```

On denaturation of the two duplexes formed, the products are:

```
         3'                                                                  5'
.... zzzzzzzzzzzzzzzzTTTTTTTTTTYYYYYYYYYYGGGGGGGGGG
newly synthesized long product 1

5'                                                                           3'
.... zzzzzzzzzzzzzzzzAAAAAAAAAAXXXXXXXXXXCCCCCCCCCCzzzzzzzzzzzzzzzz ....
original template strand+

3'                                                                  5'
.... zzzzzzzzzzzzzzzzTTTTTTTTTTYYYYYYYYYYGGGGGGGGGGzzzzzzzzzzzzzzzz ....
original template strand−

5'                                               3'
                     AAAAAAAAAAXXXXXXXXXXCCCCCCCCCCzzzzzzzzzzzzzzzz ....
                     newly synthesized long product 2
```

If these four strands are allowed to rehybridize with Primers 1 and 2 in the next cycle, the agent for polymerization will catalyze the following reactions:

```
               Primer 2      5' AAAAAAAAAA ───────────────⟶ extends to here
3' .... zzzzzzzzzzzzzzzzTTTTTTTTTTYYYYYYYYYYGGGGGGGGGG 5'
newly synthesized long product 1 extends  ⟵───────────────  GGGGGGGGGG 5'  Primer 1
5' .... zzzzzzzzzzzzzzzzAAAAAAAAAAXXXXXXXXXXCCCCCCCCCCzzzzzzzzzzzzzzzz .... 3'
original template strand+

Primer 2      5' AAAAAAAAAA ───────────────⟶ extends
3' .... zzzzzzzzzzzzzzzzTTTTTTTTTTYYYYYYYYYYGGGGGGGGGGzzzzzzzzzz .... 5'
original template strand− extends to here ⟵───────────────  GGGGGGGGGG 5'  Primer 1
           5' AAAAAAAAAAXXXXXXXXXXCCCCCCCCCCzzzzzzzzzzzzzzzz .... 3'
           newly synthesized long product 2
```

If the strands of the above four duplexes are separated, the following strands are found:

```
5' AAAAAAAAAAXXXXXXXXXXCCCCCCCCCC  3'
      newly synthesized [S+]

3' .... zzzzzzzzzzzzzzzzTTTTTTTTTTYYYYYYYYYYGGGGGGGGGG  5'
first cycle synthesized long product 1

3' .... zzzzzzzzzzzzzzzzTTTTTTTTTTYYYYYYYYYYGGGGGGGGGG  5'
newly synthesized long product 1

5' .... zzzzzzzzzzzzzzzzzAAAAAAAAAAXXXXXXXXXXCCCCCCCCCCzzzzzzzz .... 3'
original template strand+

5' AAAAAAAAAAXXXXXXXXXXCCCCCCCCCCzzzzzzzzzzzzzzzz .... 3'
             newly synthesized long product 2

3' .... zzzzzzzzzzzzzzzzTTTTTTTTTTYYYYYYYYYYGGGGGGGGGGzzzzzzzzzzzzzzzz .... 5'
``` original template strand⁻

3' TTTTTTTTTTYYYYYYYYYYGGGGGGGGGG 5'
newly synthesized [S⁻]

5' AAAAAAAAAAXXXXXXXXXXCCCCCCCCCCzzzzzzzzzzzzzzzz....3'
first cycle synthesized long product 2

It is seen that each strand which terminates with the oligonucleotide sequence of one primer and the complementary sequence of the other is the specific nucleic acid sequence [S] that is desired to be produced.

The steps of this process can be repeated indefinitely, being limited only by the amount of Primers 1 and 2, inducing agent and nucleotides present. The amount of original nucleic acid remains constant in the entire process, because it is not replicated. The amount of the long products increases linearly because they are produced only from the original nucleic acid. The amount of the specific sequence increases exponentially. Thus, the specific sequence will become the predominant species. This is illustrated in the following table, which indicates the relative amounts of the species theoretically present after n cycles, assuming 100% efficiency at each cycle:

| Number of Double Strands After 0 to n Cycles | | | |
|---|---|---|---|
| Cycle Number | Template | Long Products | Specific Sequence [S] |
| 0 | 1 | — | — |
| 1 | 1 | 1 | 0 |
| 2 | 1 | 2 | 1 |
| 3 | 1 | 3 | 4 |
| 5 | 1 | 5 | 26 |
| 10 | 1 | 10 | 1013 |
| 15 | 1 | 15 | 32,752 |
| 20 | 1 | 20 | 1,048,555 |
| n | 1 | n | $(2^n - n - 1)$ |

When a single-stranded nucleic acid is utilized as the template, only one long product is formed per cycle.

As used herein, the terms "restriction endonucleases" and "restriction enzymes" refer to bacterial enzymes of which cut double-stranded DNA at or near a specific nucleotide sequence.

The primer(s) herein may be selected by the following criteria, which are factors to be considered, but are not exclusive or determinative. First, the primers are selected from conserved regions of the AIDS genome. The gag region (nucleocapsid gene) is the most conserved of the coding regions, followed by the pol and env regions, and therefore, the gag region was chosen for initial studies.

Secondly, the primer lacks homology with any sequences of vital genomes that would be expected to compromise the test, those sequences for HTLVI, for example, being published by Seiki, M. et al., *PNAS* (USA) 80:3618–3622 (1983).

Third, the primer preferably lacks secondary structure formation in the amplified nucleic acid which may interfere with extension by the amplification enzyme such as *E. coli* DNA polymerase, preferably that portion of the DNA polymerase referred to as the Klenow fragment. This may be accomplished by employing up to about 15% by weight, preferably 5–10% by weight, dimethyl sulfoxide (DMSO) in the amplification medium and/or increasing the amplification temperatures to 30°–40° C., preferably 35°–40° C.

Fourth, the primer preferably has an approximate 50% content of guanine and cytosine, and does not contain multiple consecutive adenine and thymine residues at the 3' end of the primer which may result in less stable hybrids. Finally, if the amplified product will be detected by use of a restriction enzyme, the probe must have an internal (non-terminal) restriction site.

The oligonucleotide primers may be prepared using any suitable method, such as, for example, the phosphotriester and phosphodiester methods described above, or automated embodiments thereof. In one such automated embodiment diethylphosphoramidites are used as starting materials and may be synthesized as described by Beaucage et al., *Tetrahedron Letters* (1981), 22:1859–1862. One method for synthesizing oligonucleotides on a modified solid support is described in U.S. Pat. No. 4,458,066. It is also possible to use a primer which has been isolated from a biological source (such as a restriction endonuclease digest).

Any source of nucleic acid, in purified or nonpurified form, can be utilized as the starting nucleic acid or acids, provided it contains or is suspected of containing the specific nucleic acid sequence associated with AIDS. Thus, the process may employ, for example, DNA or RNA, including messenger RNA, which DNA or RNA may be single stranded or double stranded. In the event that RNA is to be used as a template, enzymes and/or conditions optimal for reverse transcribing the template to DNA would be utilized. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the virus-encoding gene contained in whole human DNA. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules.

The nucleic acid(s) may be obtained from any source, for example, natural DNA or RNA from higher organisms such as animals. DNA or RNA may be extracted from a bodily sample, such as blood, tissue material such as chorionic villi, or amniotic cells by a variety of techniques such as that described by Maniatis et al., *Molecular Cloning* (1982), 280–281.

If the sample is impure such as plasma, serum or blood, before amplification it may be treated with an amount of a reagent effective to open the cells, fluids, tissues, viral capsids or animal cell membranes of the sample, and to expose and/or separate the strand(s) of the nucleic acid(s). This lysing and nucleic acid denaturing step to expose and separate the strands will allow amplification to occur much more readily. In addition, the AIDS virus need not be cultivated in the sample before the sample is treated with the amplification reagents. The sample may be centrifuged to obtain buffy coats, which are then passed through a column to obtain leukocytes. The leukocytes may then be treated to extract the nucleic acids therefrom for use as the sample to be amplified.

Any specific nucleic acid sequence can be produced by the present process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater can be the specificity of the primers for the target nucleic acid sequence, and thus the greater the efficiency of the process. It will be understood that the word primer as used hereinafter may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code will be used for each strand. One primer from this collection will be substantially conserved with the end of the desired sequence to be amplified.

The specific nucleic acid sequence is produced by using the nucleic acid containing that sequence as a template. If the target nucleic acid sequence of the sample contains two strands, it is necessary to separate the strands of the nucleic acid before it can be used as the template, either as a separate step or simultaneously with the synthesis of the primer extension products. This strand separation can be accomplished using any suitable denaturing conditions, including physical, chemical or enzymatic means, the word "denaturing" used herein to include all such means. One physical method of separating the strands of the nucleic acid involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, *CSH-Quantitative Biology*, 43:63 (1978), and techniques for using RecA are reviewed in C. Radding, *Ann. Rev. Genetics* 16:405–37 (1982).

If the original nucleic acid containing the sequence to be amplified is single stranded, its complement is synthesized by adding one or two oligonucleotide primers thereto. If an appropriate single primer is added, a primer extension product is synthesized in the presence of the primer, an agent for polymerization, and the four nucleoside triphosphates described below. The product will be partially complementary to the single-stranded nucleic acid and will hybridize with the nucleic acid strand to form a duplex of unequal length strands that may then be separated into single strands as described above to produce two single separated complementary strands. Alternatively, two appropriate primers may be added to the single-stranded nucleic acid and the reaction carried out.

If the original nucleic acid constitutes the sequence to be amplified, the primer extension product(s) produced will be completely or substantially complementary to the strands of the original nucleic acid and will hybridize therewith to form a duplex of equal length strands to be separated into single-stranded molecules.

When the complementary strands of the nucleic acid or acids are separated, whether the nucleic acid was originally double or single stranded, the strands are ready to be used as a template for the synthesis of additional nucleic acid strands. This synthesis is performed under conditions allowing hybridization of primers to templates to occur. Generally it occurs in a buffered aqueous solution, preferably at a pH of 7–9, most preferably about 8. Preferably, a molar excess (for genomic nucleic acid, usually about $10^8:1$ primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP and TTP are also added to the synthesis mixture, either separately or together with the primers, in adequate amounts and the resulting solution is heated to about 90°–100° C. for from about 1 to 10 minutes, preferably from 1 to 4 minutes. After this heating period the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis reaction may occur at from room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation), which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

The newly synthesized strand and its complementary nucleic acid strand will form a double-stranded molecule under the hybridizing conditions described above if the target sequence is present, and this hybrid is used in the succeeding steps of the process. In the next step, the sample treated under hybridizing conditions is subjected to denaturing conditions using any of the procedures described above to provide single-stranded molecules if the target sequence is present.

New nucleic acid is synthesized on the single-stranded molecules. Additional agent for polymerization, nucleotides and primers may be added if necessary for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target nucleic acid sequence to the extent necessary for detection. As will be described in further detail below, the amount of the specific nucleic acid sequence produced will accumulate in an exponential fashion.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

The present invention can be performed in a stepwise fashion where after each step new reagents are added, or simultaneously, where all reagents are added at the initial step, or partially step-wise and partially simultaneous, where fresh reagent is added after a given number of steps. If a method of denaturation, such as heat, is employed which will inactivate the agent for polymerization, as in the case of a heat-labile enzyme, then it is necessary to replenish the agent after every strand separation step. The simultaneous method may be utilized when an enzymatic means is used for the strand separation step. In the simultaneous procedure, the reaction mixture may contain, in addition to the nucleic acid strand(s) containing the desired sequence, the strand-separating enzyme (e.g., helicase), an appropriate energy source for the strand-separating enzyme, such as rATP, the four nucleoside triphosphates, the oligonucleotide primers in molar excess, and the agent for polymerization, e.g., Klenow fragment of *E. coli* DNA polymerase I.

If heat is used for denaturation in a simultaneous process, a heat-stable agent such as a thermostable polymerase may be employed which will operate at an elevated temperature, preferably 50°–105° C. depending on the agent, at which temperature the nucleic acid will consist of single and double strands in equilibrium. For smaller lengths of nucleic acid, lower temperatures of about 40°–50° C. may be employed. The upper temperature will depend on the temperature at which the enzyme will degrade or the temperature above which an insufficient level of primer hybridization will occur. Such a heat-stable enzyme is described, e.g., by A. S. Kaledin et al., *Biokhimiya*, 45, 644–651 (1980). For this constant temperature reaction to succeed, the primers have their 3' ends within 6–8 base pairs of each other. Each step of the process will occur sequentially notwithstanding the initial presence of all the reagents. Additional materials may be added as necessary. After the appropriate length of time has passed to produce the desired amount of the specific nucleic acid sequence, the reaction may be halted by inactivating the enzymes in any known manner or separating the components of the reaction.

The amplification may also be carried out using a temperature-cycling reaction wherein the temperature is increased incrementally to allow for extension, annealing and denaturation using a heat-stable enzyme. This process and the enzyme and the instrument that can be used therefor are described more fully in copending U.S. application Ser. No. 899,513 filed Aug. 22, 1986, now abandoned in favor of Ser. No. 063,647, filed Jun. 17, 1987, which issued as U.S. Pat. No. 4,965,188, U.S. Pat. No. 899,241 filed Aug. 22, 1986, and 899,061 filed Aug. 22, 1986, now abandoned in favor of Ser. No. 063,509, which issued as U.S. Pat. No. 4,889,818.

The process of the present invention may be conducted continuously. In one embodiment of an automated process, the reaction may be cycled through a denaturing region, a reagent addition region, and a reaction region. In another embodiment, the enzyme used for the synthesis of primer extension products can be immobilized in a column. The other reaction components can be continuously circulated by a pump through the column and a heating coil in series, thus the nucleic acids produced can be repeatedly denatured without inactivating the enzyme.

The amplified product may be detected by analyzing it by Southern blots without using radioactive probes. In such a process, for example, a small sample of DNA from, e.g., peripheral blood lymphocytes containing a very low level of the sequence associated with AIDS is amplified, and analyzed via a Southern blotting technique. The use of non-radioactive probes is facilitated by the high level of the amplified signal.

Another method of detection involves detection using a labeled probe capable of hybridizing with the amplified nucleic acid sequence and determining if the probe has hybridized. Such probe necessarily contains a substantially conserved nucleic acid sequence from the genome of an AIDS virus (HTLVIII, ARV, LAY, LAVA, or a variant thereof) and is selected as described above for primers and amplified sequences. Preferably the probe is selected from the gag region of the AIDS genome.

One such probe method involves the oligomer restriction technique described in U.S. Pat. No. 4,683,194. In this procedure, the amplified nucleic acid is denatured and hybridized in solution to a labeled oligonucleotide probe which hybridizes specifically to the target sequence (spans the particular conserved region contained by the primers) and spans at least one restriction site of interest. The duplex formed between target land probe will reconstitute the restriction site, and when cleaved with restriction enzyme, such as, e.g., BstNI, PvuII, or DraI, releases a labeled probe fragment which can he resolved from the full-length probe by gel electrophoresis. The resulting gel is then autoradiographed. Analysis of the amplified product by this method is rapid, i.e., results can be obtained in a few hours. Preferably, the probe is 30–45 bases long and is labeled. Also, preferably the restriction enzyme is BstNI or PvuII.

Another method which may be used to analyze the amplified product is the dot blot method. In this method, the amplified samples are spotted directly on a membrane and hybridized with a labeled probe. The label may be detected by spectroscopy, photochemistry or by biochemical, immunochemical or chemical means. Examples include enzymes such as alkaline phosphatase, a radioactive label such as $^{32}P$, a fluorescent label, or biotin. In one embodiment, the probe is a biotinylated probe in which the biotin is attached to a spacer arm of the formula:

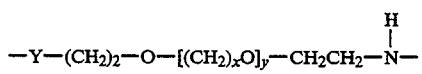

where Y is O, NH or N—CHO, x is a number from 1 to 4, and y is a number from 2 to 4. The spacer arm is in turn attached to a psoralen moiety of the formula:

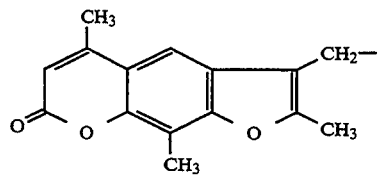

The psoralen moiety intercalates into and crosslinks a "gapped circle" probe as described by Courage-Tebbe et al., *Biochim. Biophys. Acta*, 697 (1982) 1–5, wherein the single-stranded hybridization region of the gapped circle spans the region contained between the primers. The details of this biotinylation and dot blot procedure are described more fully in commonly assigned U.S. Pat. Nos. 4,582,789 and 4,617,261, the disclosures of which are incorporated herein by reference. The biotinylated probes eliminate the need for radioactive isotopes.

Alternatively, the probe may be spotted on the membrane first under prehybridization conditions if necessary and then the amplified product is added to the pre-treated membrane under hybridization conditions, "in a reverse" dot blot format.

The dot blot procedure is more time-consuming than the oligomer restriction method described above, because the membrane must first be prehybridized and then hybridized with the probe. However, with rapidly mutating viruses, it has the advantage that sequences containing limited base mismatches are still detected under appropriate hybridizing conditions, whereas with the oligomer restriction method, any virus harboring a mutation which results in the abolishment of the restriction site will not be detected due to the variability of the virus.

The invention herein also contemplates a kit format which comprises a packaged multicontainer unit having containers of each primer and the probe utilized. The kit may also have a container with the agent for polymerization to synthesize the primer extension products, such as enzymes, a container with each of the four nucleoside triphosphates, and a container with means to detect the label (such as an avidin-enzyme complex if the label is biotin). In addition, the kit may have a container which includes a positive control containing one or more nucleic acids with a sequence of the AIDS vital genome and/or a container including a negative control without such nucleic acids. Moreover, the kit may have a container for each restriction enzyme capable of cleaving a nucleic acid containing the target sequence at a site contained in a sequence in the probe.

The following examples illustrate various embodiments of the invention and are not intended to be limiting in any respect. In the examples all parts and percentages are by weight if solid and by volume if liquid and all temperatures are in degrees Centigrade, unless otherwise indicated.

EXAMPLE 1

The desired sequences to be amplified were contained in eleven coded DNA samples obtained from Dr. Bernard Poiesz of the Regional Oncology Center, SUNY Upstate Medical Center, Syracuse, N.Y. 13210, identified as 194 BK, 342, 367,361, 368H, 207, 307,308B, 323, 326 and 340. The sequences to be amplified, the primers, and the probes were identified by the dot matrix program as described above, wherein the sequence window selected was at least 20 base pairs long, so that the sequences were chosen within conserved regions of the AIDS viruses.

The coded samples were first cultured in the presence of interleukin-2 by Dr. Poeisz to test for the presence of virus. Then, the DNA was extracted from the samples by the following procedure:

1. $1$–$2 \times 10^8$ cultured cells were lysed in tubes with 20 ml of sodium dodecyl sulfate lysis buffer (1% SDS, 150 mM NaCl, 25 mM $Na_2$ EDTA).
2. 400 μl of a 5 mg/μl solution of proteinase K was added per tube and incubated at 37° C. overnight.
3. The DNA was sequentially extracted with phenol, and $CHCl_3$:isoamyl alcohol followed by precipitation with ethanol.
4. The DNA was spooled out on a glass rod and resuspended in $1 \times TE$ buffer (10 nM Tris, 1 mM $Na_2EDTA$, pH 7.5) and dialyzed exhaustively against $1 \times TE$ buffer.

I. Synthesis of Primers

The following two oligodeoxyribonucleotide primers, designated SK01 and SK02, respectively, were prepared by the method described below:

| | |
|---|---|
| 5'-CAGGGAGCTAGAACGAT-3' | (SK32) |
| 5'-CTTCTGATCCTGTCTGA-3' | (SK33) |

(SK01 and SK02 were selected to provide for amplification of 107 bases between nucleotides 900 and 1006 of HTLVIII-isolate BH10.)

A. Automated Synthesis Procedures: The diethylphosphoramidites, synthesized according to Beaucage and Caruthers (*Tetrahedron Letters* (1981) 22:1859–1862) were sequentially condensed to a nucleoside derivatized controlled pore glass support using a Biosearch SAM-1. The procedure included detritylation with trichloroacetic acid in dichloromethane, condensation using benzotriazole as activating proton donor, and capping with acetic anhydride and dimethylaminopyridine in tetrahydrofuran and pyridine. Cycle time was approximately 30 minutes. Yields at each step were essentially quantitative and were determined by collection and spectroscopic examination of the dimethoxytrityl alcohol released during detritylation.

B. Oligodeoxyribonucleotide Deprotection and Purification Procedures: The solid support was removed from the column and exposed to 1 ml concentrated ammonium hydroxide at room temperature for four hours in a closed tube. The support was then removed by filtration and the solution containing the partially protected oligodeoxynucleotide was brought to 55° C. for five hours. Ammonia was removed and the residue was applied to a preparative polyacrylamide gel. Electrophoresis was carried out at 30 volts/cm for 90 minutes after which the band containing the product was identified by UV shadowing of a fluorescent plate. The band was excised and eluted with 1 ml distilled water overnight at 4° C. This solution was applied to an Altech RP18 column and eluted with a 7–13% gradient of acetonitrile in 1% ammonium acetate buffer at pH 6.0. The elution was monitored by UV absorbance at 260 nm and the appropriate fraction collected, quantitated by UV absorbance in a fixed volume and evaporated to dryness at room temperature in a vacuum centrifuge.

C. Characterization of oligodeoxyribonucleotides: Test aliquots of the purified oligonucleotides were $^{32}$P labeled with polynucleotide kinase and $\gamma$-$^{32}$P-ATP. The labeled compounds were examined by autoradiography of 14–20% polyacrylamide gels after electrophoresis for 45 minutes at 50 volts/cm. This procedure verifies the molecular weight. Base composition was determined by digestion of the oligodeoxyribonucleotide to nucleosides by use of venom diesterase and bacterial alkaline phosphatase and subsequent separation and quantitation of the derived nucleosides using a reverse phase HPLC column and a 10% acetonitrile, 1% ammonium acetate mobile phase.

II. Amplification Reaction

One microgram of DNA from each of the eleven coded DNA samples from Dr. Poiesz was added to 100 $\mu$l of buffer consisting of 10 mM Tris-HCl, pH 7.5, 50 nM sodium chloride and 10 nM magnesium chloride and containing 100 picomoles of Primer SK01, 100 picomoles of Primer SK02, and 150 nanomoles each of dATP, dCTP, dGTP and TTP.

The resulting solution was heated to 100° C. for 10 minutes and allowed to cool to room temperature for two minutes, whereupon 2 $\mu$l containing one unit of Klenow fragment of E. coli DNA polymerase was added. The reaction was allowed to proceed for two minutes at room temperature, after which the enzyme was inactivated by heating at 95° C. for two minutes. The denaturation, primer annealing, and extension with Klenow, two minutes per step, and adding polymerase were repeated nineteen times.

III. Synthesis and Phosphorylation of Oligodeoxyribonucleotide Probe

A labeled DNA probe, SK03, of the sequence:

5-*AATCCTGGCCTGTTAGAAACAT-CAGAAG-3', where * indicates the label, was synthesized according to the procedures described in Section I. The probe was labeled by contacting 10 pmole thereof with 4 units of T4 polynucleotide kinase (New England Biolabs) and 50 pmole $\gamma$$^{32}$P-ATP (New England Nuclear, about 7200 Ci/mmole) in a 40 $\mu$l reaction volume containing 70 mM Tris buffer (pH 7.6), 10 nM MgCl$_2$, 1.5 nM spermine, and 2.5 mM dithiothreitol for 90 minutes at 37° C. The total volume was then adjusted to 100 $\mu$l with 25 mM EDTA and an aliquot removed for determination of specific activity by TCA precipitation. The labeled probe was concentrated using Speed-vac and purified by electrophoresis on a 18% polyacrylamide gel (19:1 acrylamide:BIS,. Bio-Rad) in Trisboric acid-EDTA (TBE) buffer (89 nM Tris, 89 mM boric acid, 2.5 mM EDTA, pH 8.3) at 500 volts for one hour. After localization by autoradiography, the portion of the gel containing the labeled probe was excised, crushed and eluted into 0.2 ml TE buffer overnight at 4° C. TCA precipitation of the reaction product indicated that the specific activity was 2 Ci/mmole and the final concentration was 20 pmole/ml.

IV. Hybridization/Digestion of Amplified Genomic DNA with Probe and BstNI

Ten microliters of amplified DNA (containing the preamplification equivalent of 71 $\mu$g of genomic DNA) was dispensed into a 1.5 ml Microfuge tube and 20 $\mu$l of TE buffer to a final volume of 30 $\mu$l. The sample was denatured at 95° C. for 10 minutes. Ten microliters of 0.6 M NaCl containing 0.02 pmole of SK03 probe was added to the tube, mixed gently, overlayed with mineral oil, and immediately transferred to a 56° C. heat block for one hour. Ten microliters of 50 nM MgCl$_2$ and 1 $\mu$l of BstNI (10 units, New England Biolabs) were added and the reannealed DNA was digested for 30 minutes at 56° C. The reaction was stopped by adding 4 $\mu$l 75 mM EDTA and 6 $\mu$l tracking dye to a final volume of 60 $\mu$l.

The mineral oil was extracted with 0.2 ml chloroform, and 13 $\mu$l of the reaction mixture (~15 ng genomic DNA) was loaded onto a 30% polyacrylamide mini-gel (19:1, Bio-Rad) in a Hoeffer SE200 apparatus. The gel was electrophoresed at approximately 300 volts for one hour until the bromphenol blue dye front migrated to 3.0 cm off origin. The top 1.5 cm of the gel was removed and the remaining gel was exposed at least overnight with two intensification screens at −70° C.

V. Discussion of Results

The autoradiograph showed that the AIDS DNA sequence was only present in sample 368H, which was later found to be the only HTLVIII positive DNA. The other ten samples were as follows: (a) 194BK=DNA from leukemia patient (no virus isolated), (b) 342=HTLVI, (c) 367=HTLVI, (d) 361 HTLVI, (e) 207=patient with aggressive leukemia (skin involvement), (f) 307=HTLVI prototype cell line (highest vital DNA to date), (g) 308=HTLVI, (h) 323=HTLVII, (i) 326=HTLVI, and (j) 340=patient with aggressive leukemia (different from (e)).

Therefore, the primers employed were able to amplify the DNA to allow the probe to detect accurately the sequence. The other sables remained negative even with ten additional cycles of amplification. Amplification in the presence of 10% DMSO (minimizes secondary structure formation) at 37° C. also indicated the HTLVIII sample as the only positive sample.

EXAMPLE 2

In this example, the same procedure was followed as described in Example 1 except that the primers employed, designated SK24 and SK18, were as follows:

5'-ATCCCAGTAGGAGAA-3'    (SK24)

5'-TTATGTCCAGAATGC-3'    (SK18)

An alternative to SK24 was the primer SK25 as follows:
5'-ATAATCCACCTATCCCAG-3'    (SK25)

The probe employed, SK19, was of the sequence:
5'-*ATCCTGGGATTAAATAAAATAG-
TAAGAATGTATAGCCCTAC-3', where * indicates the label. The probe was labeled as described in Section III. SK24 and SK18 were selected to provide for the amplification of a hydrophilic region of gag from nucleotides 1552 to 1642 of HTLVIII. SK25 and SK18 were selected to provide for amplifying a hydrophilic region of gag from nucleotides 1541 to 1642 of HTLVIII. SK19, when annealed to the amplified DNA, reconstitutes a BstNI site. Digestion with this enzyme releases a 4-mer.

The autoradiograph for hybridization and restriction at 53° C. showed as positive only the HTLVIII sample found in Example 1. A background band appearing in all samples disappeared when the temperature of hybridization and restriction was raised to 60° C. from 53° C. The increased temperature is presumed to have minimized nonspecific hybridization of the probe.

EXAMPLE 3

A 180 bp DNA fragment which encodes a hydrophilic region of gag (nucleotides 1470–1649 of HTLVIII-isolate BH10), having 186 base pairs including BamHI ends, was constructed by first ligating 10 overlapping oligomers using T4 DNA ligase. The oligomers are shown in FIG. 2. The resulting fragment was then cloned into the BamHI site of M13mp10w which is commercially available. None of the clones sequenced had the exact desired sequence. However, using two clones shown in FIG. 3 (where X denotes a mutation in the gene), a clone with the correct sequence was constructed by substituting the SpeI/BstXI fragment of clone M13mp10:C7 with the SpeI/BstXI fragment of clone M13mp10W:D6. DNA from M13mp10W:C7 was digested with SpeI and BstXI, treated with alkaline phosphatase and the larger vector containing fragment purified from an agarose gel. The SpeI/BstXI DNA fragment from clone M13mp10W:D6 was purified from a polyacrylamide gel after double digestions with the same enzymes. The purified fragments from M13mp10W:C7 and M13mp10W:D6 were ligated and transformed into E. coli strain DG98 available from the American Type Culture Collection. The resulting clone, designated M-13-GAG, contains the correct sequence and was deposited with the ATCC on Jan. 8, 1986 with ATCC No. 40,218.

This M-13-GAG may be used to construct a gapped circle probe as described above to evaluate an amplified sample in a non-isotopic dot blot format.

The amplified product may be prepared from two primers, SK23 and SK28, which encompass the entire 180 mer in M-13-GAG and have the following sequence:

5'-ATGAGAGAACCAAGG-3'    (SK23)

5'-CCTTGTCTTATGTCCAG-3'    (SK28)

These primers, which were selected to amplify between nucleotides 1468 and 1649, were already tested with probe SK19 and found to detect the HTLVIII sample successfully.

EXAMPLE 4

Seventy-one coded samples, the DNA of which was extracted by Dr. Poiesz using the method described in Example 2 were initially analyzed by their DNA using the primer pair of SK01 and SK02 of Example 1 or SK17 and SK18, where SK18 is defined in Example 2 and SK17 has the sequence:

5'-CCAGTAGGAGAAAT-3' which is selected to amplify the hydrophilic region of gag from nucleotides 1555 to 1642 of HTLVIII. The amplification using the primer pair SK17 and SK18 was carried out in the presence of 10% DMSO by weight at 37° C., but otherwise according to the procedure of Example 1. After amplification the procedure of Example 1 was used to detect the DNA, using the probe SK03 (of Example 1) or SK19 (of Example 2). Some of the ambiguous samples were further analyzed using the primer pair SK24 and SK18 of Example 2 and using the probe SK19 at room temperature.

The results show that all samples which were identified as positive by the test herein were DNAs isolated from AIDS or ARC patients, including a HTLVIII isolate, a LAV isolate and an AIDS-associated virus (AAV) identified by Dr. Poiesz. In addition, an antibody positive, reverse transcriptase negative, healthy homosexual who has had multiple contacts with AIDS victims was also identified as positive by both sets of primer pairs. The SK17-SK18 and SK24-SK18 primer pairs appeared to detect more positives than the SK01-SK02 primer pair.

None of the negative control samples (normal T cells, uninfected cell lines or HTLVII) showed positively in the assays herein. The test herein identified ten infected samples as positive which were negative by reverse transcriptase. On the other hand, five samples which were reverse transcriptase positive (3 out of the 5 were ±) were negative by the test herein. All 71 samples proved to be ELISA .positive, showing that ELISA is not a very discriminative or specific test for the AIDS virus.

The above examples show that AIDS vital DNA sequences can be identified in cell lines infected with blood, semen mononuclear cells, and semen supernatants from patients with AIDS or ARC.

EXAMPLE 5

This example illustrates that the technique herein can be applied directly to the identification of AIDS vital DNA sequences in peripheral mononuclear cells of fresh blood without having to cultivate the virus first.

Coded blood samples from AIDS patients were treated as follows by Dr. Poeisz: First, they were centrifuged using low-speed centrifugation (about 300× g) to pellet all the cells, thereby obtaining bully coats. The bully coats were passed through a Ficoll-Hypaque density column and the leukocytes were collected from the column. The DNA was extracted from the leukocytes by the procedure described in Example 1.

The DNA was amplified using the primer pairs SK17 and SK18 described in Examples 2 and 4, respectively, in the presence of 10% DMSO by weight at 37° C. using the procedure described in Example 1 with 1 unit, 2 units and 4 units of Klenow fragment. After amplification, the probes used, following the procedure of Example 1, were either SK03 (of Example 1) or SK19 (of Example 2). Some of the ambiguous samples were further analyzed using the primer pair SK24 and SK18 of Example 2 and the probe SK19 at room temperature.

The results after overnight exposure show that the DNAs isolated from some of the AIDS or ARC patients were identified as positive.

The experiment was repeated using primer pairs SK23 and SK28 (described in Example 3), and probe SK19 (Example 2). The experiment was again repeated using primer pairs SK32 and SK33 having the sequences as follows:

| | |
|---|---|
| 5'-ACCTGCCACCTGTAGTAG-3' | (SK32) |
| 5'-GCCATATTCCTGGACTACAG-3' | (SK33) | and using the probe SK34 of the sequence:

| | |
|---|---|
| 4'-TAGTAGCCAGCTGTGATAAATGTCAGC-TAAAAGGAGAAGCC-3' | (SK34) |

The restriction enzyme PvuII was used to cleave the restriction site of SK34.

The results from both experiments after a 6-day exposure period revealed that the DNAs isolated from some of the AIDS or ARC patients were identified as positive.

The following deposit was made on the date given:

| Strain | Deposit Date | ATCC No. |
|---|---|---|
| M13-GAG | January 8, 1986 | 40,218 |

This deposit was made under the provisions of the Budapest Treaty on the International Recognition of the Deposit of Microorganisms for the Purposes of Pat. Procedure and the Regulations thereunder (Budapest Treaty). This assures maintenance of a viable culture for 30 years from date of deposit. The organism will be made available by ATCC under the terms of the Budapest Treaty, and subject to an agreement between applicants and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application agrees that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

Those skilled in the art should note that the disclosure herein on particular embodiments of the present invention is exemplary only, and that various other alternative, adaptations, and modifications may be made within the scope of the present invention. Accordingly, the present invention is not limited to the specific embodiments as illustrated herein, and is embodied in the claims appended thereto.

What is claimed is:

1. A pair of oligonucleotide primers for a polymerase chain reaction, which primers are sufficiently complementary to conserved regions among the nucleic acid sequences of AIDS viruses to hybridize therewith and not sufficiently complementary to HTLVI nucleic acids to hybridize therewith, wherein said conserved regions are at least 20 nucleotides long, wherein said primer pair consists of a member that comprises a nucleic acid sequence at least 14 nucleotides in length, which nucleic acid sequence is contained within a sequence selected from the group of nucleic acid sequences consisting of
5'-ATGAGAGAACCAAGG-3',
5'-CCAGTAGGAGAAAT-3',
5'-ATCCCAGTAGGAGAA-3',
and 5'-ATAATCCACCTATCCCAG-3',
and a member that comprises a nucleic acid sequence at least 14 nucleotides in length, which nucleic acid sequence is contained within a sequence selected from the group of nucleic acid sequences consisting of
5'-CCTTGTCTTATGTCCAG-3', and 5'-TTATGTCCAGAATGC-3'.

2. An oligonucleotide primer comprising a nucleic acid sequence which sequence is sufficiently complementary to a substantially conserved region among the nucleic acid sequences of AIDS viruses, and specific to the nucleic acids of AIDS viruses, to hybridize therewith and act as a point of initiation of synthesis in an amplification reaction, wherein said primer is selected from the group consisting of:
5'ATGAGAGAACCAAGG-3',
5'-CCTTGTCTTATGTCCAG-3',
5'-CCAGTAGGAGAAAT-3',
5'-ATCCCAGTAGGAGAA-3',
5'-TTATGTCCAGAATGC-3', and 5'-ATAATCCACCTATCCCAG-3'.

3. A DNA probe for detecting or monitoring amplified AIDS virus nucleic acids in a sample capable of hybridizing to an AIDS virus nucleic acid sequence, wherein said probe consists of a nucleic acid sequence between 28 and 180 nucleotides in length, which probe nucleic acid sequence contains a subsequence at least 28 nucleotides in length of a sequence selected from the group of nucleic acid sequences consisting of:
5-ATCCTGGGATTAAATAAAATAG-TAAGAATGTATAGCCCTAC-3',
5-GATCCGAGAGAACCAAGGGGAAGT-GACATAGCAGGAACTACTAGTACCCTT-CAGGAACAAATAGGATGGAT-GACAAATAATCCACCTATCCCAGTAG-GAGAAATCTATAAAGATG-GATAATCCTGGGATTAAATAAAATAG-TAAGAATGTATAGCCCTACCAG-CATTCTGGACATAAGACAAGGG-3', and the sequences fully complementary thereto, and wherein said probe, when hybridized to its complementary sequence, encompasses a restriction enzyme cleavage site.

4. A DNA probe according to Claim 3 comprising a nucleic acid sequence, or a sequence fully complementary to a sequence selected from the group consisting of:
5'-AATCCTGGCCTGTTTAGAAACAT-CAGAAG-3',
5'-TAGTAGCCAGCTGTGATAAATGTCAGC-TAAAAGGAGAAGCC-3',
5-ATCCTGGGATTAAATAAAATAG-TAAGAATGTATAGCCCTAC-3', and
5'-GATCCGAGAGAACCAAGGGGAAGT-GACATAGCAGGAACTACTAGTACCCTT- CAGGAACAAATAGGATGGATGACAAATAATCCACCTATCCCAGTAGGAGAAATCTATAAAGATGGATAATCCTGGGATTAAATAAAATAGTAAGAATGTATAGCCCTACCAGCATTCTGGACATAAGACAAGGG-3'.

5. A DNA probe according to claim 3 consisting of a nucleotide sequence between 30 and 45 nucleotides long that is fully complementary to 5'-GATCCGAGAGAACCAAGGGGAAGTGACATAGCAGGAACTACTAGTACCCTTCAGGAACAAATAGGATGGATGACAAATAATCCACCTATCCCAGTAGGAGAAATCTATAAAGATGGATAATCCTGGGATTAAATAAAATAGTAAGAATGTATAGCCCTACCAGCATTCTGGACATAAGACAAGGG-3' or the sequence that is fully complementary thereto.

6. A DNA probe according to claim 5, wherein said restriction enzyme cleavage site is a BstNI site.

7. A pair of oligonucleotide primers for a polymerase chain reaction consisting of a first and a second primer which are sufficiently complementary to conserved regions among the nucleic acid sequences of AIDS viruses to hybridize therewith and not sufficiently complementary to HTLVI nucleic acids to hybridize therewith, wherein each member of said pair of primers consists of a nucleic acid sequence at least 14 nucleotides in length, wherein said first primer sequence is contained in the target sequence 5'-GATCCGAGAGAACCAAGGGGAAGTGACATAGCAGGAACTACTAGTACCCTTCAGGAACAAATAGGATGGATGACAAATAATCCACCTATCCCAGTAGGAGAAATCTATAAAGATGGATAATCCTGGGATTAAATAAAATAGTAAGAATGTATAGCCCTACCAGCATTCTGGACATAAGACAAGGG-3', and wherein said second primer sequence is contained in the sequence that is fully complementary to said target sequence.

8. A DNA probe for detecting amplified AIDS virus nucleic acids in a sample, wherein said probe is capable of hybridizing to an AIDS virus nucleic acid sequence, and wherein said probe is selected from the group consisting of:

5-ATCCTGGGATTAAATAAAATAGTAAGAATGTATAGCCCTAC-3', and

5'-GATCCGAGAGAACCAAGGGGAAGTGACATAGCAGGAACTACTAGTACCCTTCAGGAACAAATAGGATGGATGACAAATAATCCACCTATCCCAGTAGGAGAAATCTATAAAGATGGATAATCCTGGGATTAAATAAAATAGTAAGAATGTATAGCCCTACCAGCATTCTGACATAAGACAAGGG-3'.

* * * * *

UNITED STATES PATENT AND TRADEMARK OFFICE
CERTIFICATE OF CORRECTION

PATENT NO. : 5,386,022

DATED : January 31, 1995

INVENTOR(S) : John J. Sninsky and Shirley Y. Kwok

It is certified that error appears in the above-identified patent and that said Letters Patent is hereby corrected as shown below:

On the cover page, item No. 54, line 1, please delete "PRIMES" and insert therefor --PRIMERS--.

On the cover page, line No. 75, line 2, please delete "Calif.;" and insert therefor --Calif.--.

On the cover page, item No. 75, lines 3-5, please delete "David Mack, Chicago, Ill.; Henry A. Erlich, Oakland; Kary B. Mullis, La Jolla, both of Calif.--

On the cover page, under the section entitled "Other Publications," line 12, please delete "Starich" and insert therefor --Starcich--.

In column 1, line 1, please delete "PRIMES" and insert therefor --PRIMERS--.

In column 6, line 51, please delete ""[$S^{31}$]" and insert therefor --[$S^-$]--.

In column 9, line 55, please delete "vital" and insert therefor --viral--.

In column 12, line 61, please delete "which-will" and insert therefor --which will--.

In column 15, line 4, please delete "land" and insert therefor --and--.

In column 15, line 8, please delete "he" and insert therefor --be--.

In column 16, line 11, please delete "vital" and insert therefor --viral--.

In column 16, line 55, please delete "(SK32)" and insert therefor --(SK01)--.

In column 16, line 56, please delete "(SK33)" and insert therefor --(SK02)--.

In column 18, line 5, both occurrences, please delete "nM" and insert therefor --mM--.

UNITED STATES PATENT AND TRADEMARK OFFICE
CERTIFICATE OF CORRECTION

PATENT NO. : 5,386,022

DATED : January 31, 1995

INVENTOR(S) : John J. Sninsky and Shirley Y. Kwok

It is certified that error appears in the above-identified patent and that said Letters Patent is hereby corrected as shown below:

In column 18, line 30, please delete "nM" and insert therefor --mM--.

In column 18, line 50, please delete "361 HTLVI," and insert therefor --361=HTLVI--.

In column 18, line 53, please delete "vital" and insert therefor --viral--.

In column 18, line 58, please delete "sables" and insert therefor --samples--.

In column 20, line 32, please delete "pal r" and insert therefor --pair--.

In column 20, line 40, please delete ".positive" and insert therefor --positive--.

In column 20, line 43, please delete "vital" and insert therefor --viral--.

In column 20, line 50, please delete "vital" and insert therefor --viral--.

In column 20, line 56, please delete "bully" and insert therefor --buffy--.

In column 20, line 57, please delete "bully" and insert therefor --buffy--.

UNITED STATES PATENT AND TRADEMARK OFFICE
CERTIFICATE OF CORRECTION

PATENT NO. : 5,386,022
DATED : January 31, 1995
INVENTOR(S) : John J. Sninsky and Shirley Y. Kwok It is certified that error appears in the above-indentified patent and that said Letters Patent is hereby corrected as shown below:

In column 22, Claim 4, please delete lines 4-7.

In column 24, Claim 8, line 15, please delete after "CATTCTG" please insert --G--.

Signed and Sealed this

Thirteenth Day of June, 1995

*Attest:*

BRUCE LEHMAN

*Attesting Officer*  *Commissioner of Patents and Trademarks*